(12) United States Patent
Pisharodi (10) Patent No.: US 6,989,013 B2
(45) Date of Patent: Jan. 24, 2006

(54) MEDICAL APPLIANCE FOR BRIDGING AND STABILIZING SPACED APART BONE SEGMENTS HAVING A BONE SCREW LOCKING SYSTEM

(75) Inventor: Madhavan Pisharodi, Brownsville, TX (US)

(73) Assignee: Perumala Corporation, (KY)

( * ) Notice: Subject to any disclaimer, the term of this patent is extended or adjusted under 35 U.S.C. 154(b) by 217 days.

(21) Appl. No.: 10/419,413

(22) Filed: Apr. 21, 2003

(65) Prior Publication Data
US 2004/0030340 A1 Feb. 12, 2004

Related U.S. Application Data

(63) Continuation-in-part of application No. PCT/US01/29915, filed on Sep. 25, 2001.

(51) Int. Cl.
*A61B 17/56* (2006.01)

(52) U.S. Cl. ..................................................... 606/71
(58) Field of Classification Search ................. 606/72, 606/71, 70, 73, 60, 61, 69; 411/338
See application file for complete search history.

(56) References Cited

U.S. PATENT DOCUMENTS

| | | | |
|---|---|---|---|
| 4,892,545 A | 1/1990 | Day et al. | |
| 5,123,926 A | 6/1992 | Pisharodi | |
| 5,458,641 A | 10/1995 | Ramirez Jimenez | |
| 5,531,746 A * | 7/1996 | Errico et al. | 606/61 |
| 5,549,612 A | 8/1996 | Yapp et al. | |
| 5,616,144 A | 4/1997 | Yapp et al. | |
| 5,810,816 A | 9/1998 | Roussouly et al. | |
| 5,951,557 A * | 9/1999 | Luter | 606/69 |
| 6,030,389 A | 2/2000 | Wagner et al. | |
| 6,193,721 B1 | 2/2001 | Michelson | |
| 6,454,770 B1 * | 9/2002 | Klaue | 606/69 |
| 6,575,975 B2 * | 6/2003 | Brace et al. | 606/69 |
| 6,589,244 B1 * | 7/2003 | Sevrain et al. | 606/72 |

* cited by examiner

*Primary Examiner*—Pedro Philogene
(74) *Attorney, Agent, or Firm*—Jackson Walker, LLP (57) ABSTRACT

A locking system for attaching a first workpiece to a bone or second workpiece. A countersink in the first workpiece has an opening for receiving a screw having a threaded first end, an opposite top head end, and a collar. The collar has external threads which engage complimentary threads in the counter sink. The collar is sized to allow the screw head to rotate within a smooth concave cavity in the collar while at the same time retaining the screw within the collar. Once the screw is threaded into the bone (or second workpiece), the collar retains the screw securely in the first workpiece.

6 Claims, 7 Drawing Sheets

MEDICAL APPLIANCE FOR BRIDGING AND STABILIZING SPACED APART BONE SEGMENTS HAVING A BONE SCREW LOCKING SYSTEM

This application is a continuation-in-part application based upon PCT Application Ser. No. PCT/US01/29915, filed Sep. 25, 2001, which claims priority to U.S. patent Ser. No. 09/746,750, filed Dec. 21, 2000, now U.S. Pat. No. 6,402,755, issued Jun. 11, 2002.

BACKGROUND OF THE INVENTION

The present invention relates to a medical appliance, and, more particularly, to a medical appliance for bridging and stabilizing spaced apart bone segments. Even more specifically, the present invention relates to a bone screw locking system for use with a medical appliance.

While the present invention is intended for use with vertebrae, it should be understood that any spaced apart bone segment may utilize the present invention.

Treatment of a herniated disk in the neck and in the lumbar region continues to be a challenging field of medicine. The classical treatment for a ruptured disk continues to be removal of the disk from between the vertebrae. By this process of removing the disk, overall spinal instability is increased. This may aggravate the patient to some degree after the operation. Another procedure previously employed is to replace the disk space with a bone graft, bringing about fusion of the vertebrae above and below the disk, eliminating the empty space between the vertebrae and improving stability.

Theoretically a diskectomy with fusion is a satisfactory procedure, though not ideal because the replaced bone does not have the principal functions of the cartilage tissue of the disk. This fusion procedure is technically demanding and has medical complications because of several physiological factors.

It must be remembered that the disk primarily serves as a mechanical cushion while permitting limited mobility. For any replacement system for a disk to be truly effective, it must allow for mobility within the natural limits of the original disk. In other words, the replacement should match appropriate joint rheology (movement behavior). The natural disk allows about 11 degrees of flexion-extension, limited lateral bending of 3 to 5 degrees, and very restricted rotation of about 1 degree. Further, any replacement system must be affixed to existing good, healthy bone in a manner that is not likely to loosen. An otherwise successful therapy is of little value if the appliance becomes loosened after the operation.

Various prosthetic devices and implants are disclosed in the art, but all are characterized by compromises to the full functions of a natural disk discussed above. Examples of the prior art include the following U.S. Pat. Nos.: 5,893,890; 5,693,100; 5,658,336; 5,653,761; 5,653,762; 5,390,683; 5,171,278; and 5,123,926. The specification and drawings of U.S. Pat. No. 6,402,755 are herein incorporated by reference.

The present invention provides a bone screw locking system for use in stabilization of spaced apart bone segments while still allowing some flexion and rearward extension of the bones with some lateral displacement. The present invention is particularly useful to stabilize adjacent vertebrae in the human spine. Again, the unique screw locking system of the present invention may be used in a medical appliance which requires joining or holding two workpieces or two separate members together.

SUMMARY OF THE INVENTION

Accordingly, the present invention provides a screw locking system for medical appliances and particularly for bridging and stabilizing spaced apart bone segments. A rigid, elongate bottom plate to span space between bone segments and to attach to a ledge surface of each bone such that a plurality of screw barrels rotatably engaging a plurality of openings in the bottom plate base may receive a plurality of barrel screws to couple the bottom plate to a rigid, elongate top plate.

The top plate is also equipped with a plurality of countersinks. The countersinks receive bone screws such that the top plate may be attached to the outside surface of each bone segment. The present invention has a unique fastener/locking member disposed in the countersink for securing the bone screws to the medical appliance such that axial and rotational movement of the bone screws is restricted.

The screw barrels of the present invention may be equipped with an angled first end and a riveted second end such that movement of the screw barrels may be restricted in a first and second direction while still allowing the screw barrels to rotate within the openings to allow the barrel screws to engage the screw barrels at various angles. In one embodiment, a locking ring having a plurality of tapered rachet teeth on an interior surface is used to secure the bone screws to the medical appliance. The teeth engage a serrated neck of each bone screw upon insertion of each bone screw into a countersink, thus securing the bone screws.

The configuration of each locking ring and each countersink may vary depending on the application of the medical appliance. They may have a substantially circular configuration or a non-circular configuration that allow them to work in concert to provide varying degrees of axial and rotational movement for the bone screws.

DETAILED DESCRIPTION OF THE PREFERRED EMBODIMENT

The present invention, described herein, is used in conjunction with a medical appliance (100) adapted to bridge and stabilize spaced apart bone segments (10A and 10B, respectively). The present invention is a locking system for attaching a medical appliance to bone. Referring to the Figures, the spaced apart bone segments (10A and 10B, respectively) have outside surfaces (12A and 12B, respectively), ledge surfaces (14A and 14B, respectively), and inside surfaces (16A and 16B, respectively). Each ledge surface is a prepared surface used for the attachment of the bottom plate (18) to the bone segments (10A and 10B, respectively).

Figure 1:
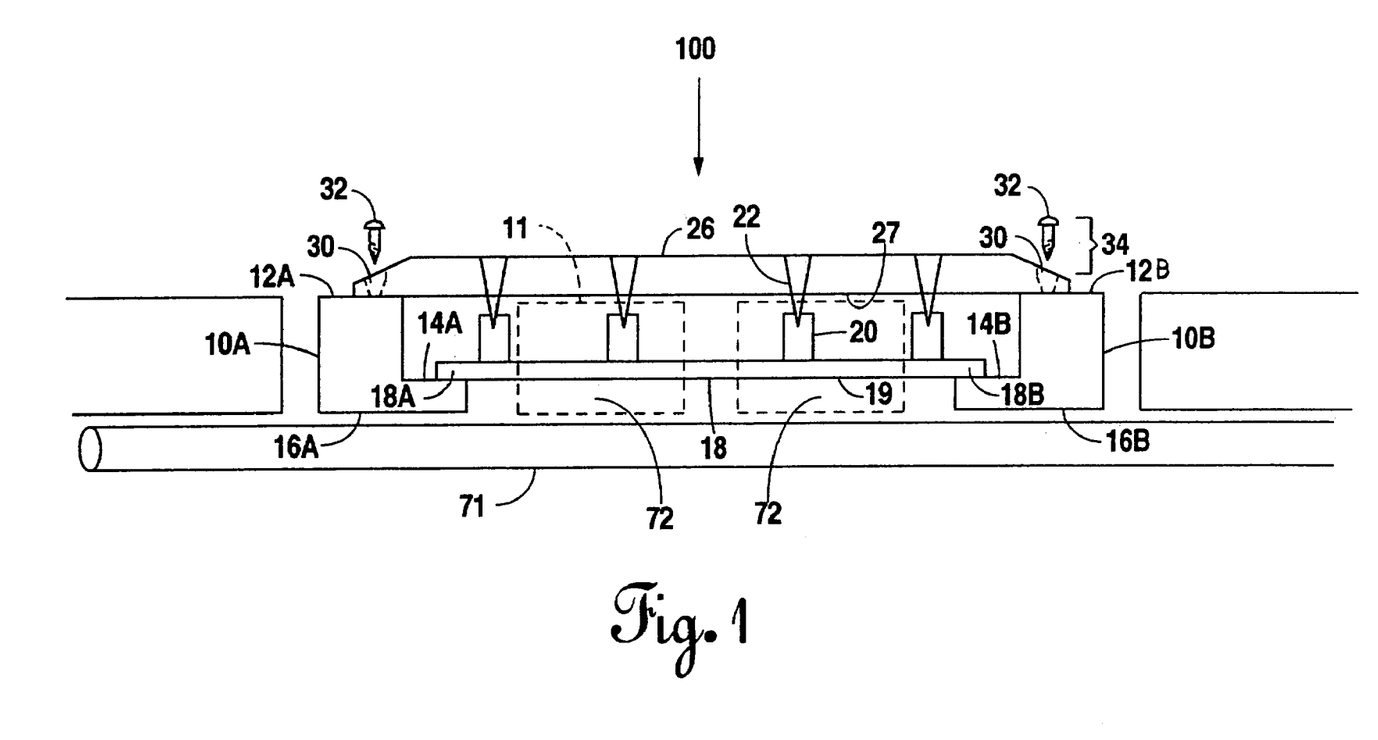
FIG. 1 is a side elevation view of a portion of the human spinal column having a preferred embodiment of the medical appliance of the present invention inserted therein.

One embodiment of the present invention is shown in FIG. 1 with an appliance implanted into the human spinal column. The medical appliance (100) is implanted into space between bone segments (10A and 10B, respectively) from which a portion of the vertebral body along with the intervertebral disk (11) has been removed, i.e. by diskectomy with corpectomy. The medical appliance has a bottom plate (18), a top plate (26), and a locking member (34).

Figure 2:
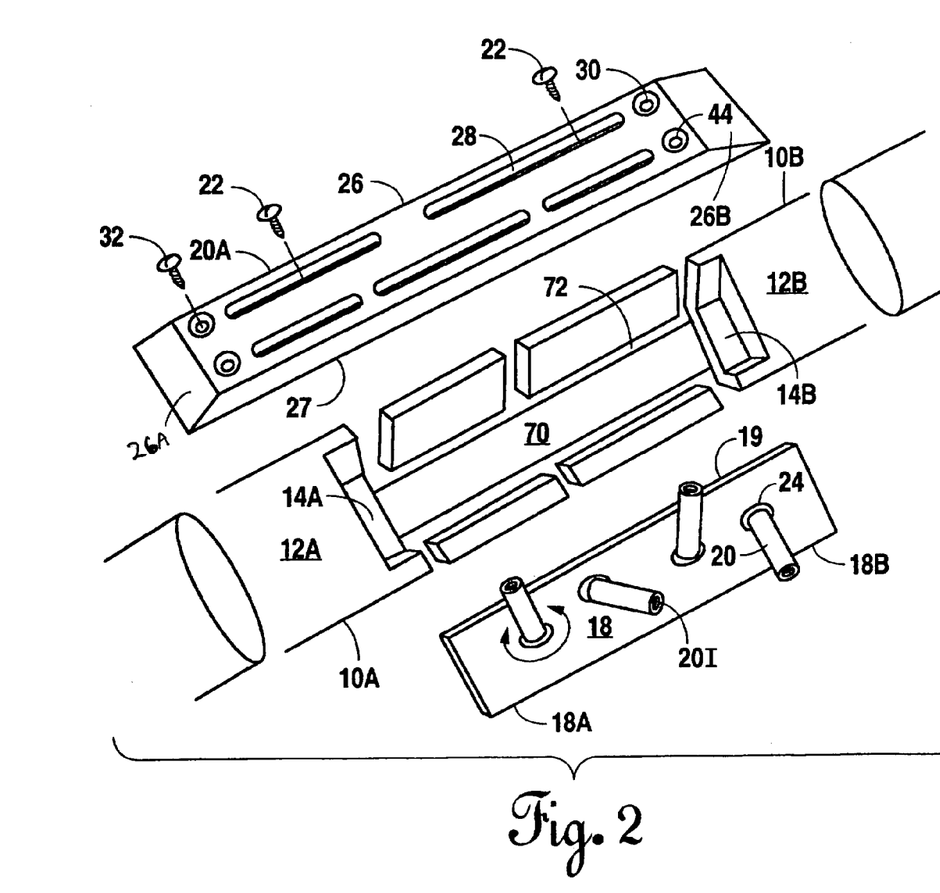
FIG. 2 is an exploded perspective view of a portion of the human spinal column having a preferred embodiment of the medical appliance of the present invention prior to attachment.

Referring to FIGS. 1 and 2, the bottom plate (18) is a rigid, elongate plate for spanning space (72) between bone segments (10A and 10B, respectively) and is attachable to the ledge surfaces (14A and 14B, respectively) of the bone segments. The bottom plate (18) has a bottom plate base (19) having a plurality of openings (24) for rotatably retaining a plurality of screw barrels (20). The screw barrels are substantially cylindrical in shape and extend from the bottom plate base (19) in a first direction. This first direction is away from the spinal cord (70) of the patient (not shown) such that the screw barrels may receive a barrel screw (22), as described below.

The medical appliance (100) has a rigid, elongate top plate (26) having a top plate base (27). The top plate base has a plurality of slots (28) (FIG. 2) for receiving a plurality of barrel screws (22). The slots (28) are positioned and aligned upon the top plate base (27) such that barrel screws may be placed through the slots of the top plate (26) so they may extend in a second direction. This second direction is in the direction of the spinal cord (70), as shown in FIG. 1. This allows each barrel screw to engage a threaded inner surface (201) of each screw barrel (20) such that the top plate (26) and the bottom plate (18) may be fastened together. This allows the top and bottom plate to act in concert to bridge and stabilize the spaced apart bone segments (10A and 10B, respectively).

Figure 2A:
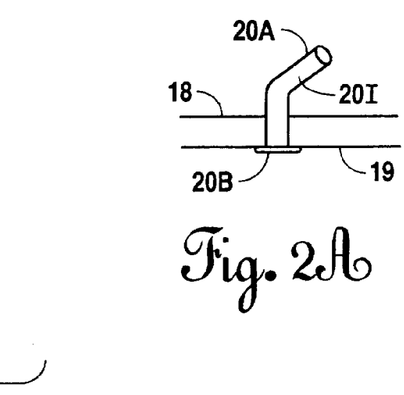
FIG. 2A is a side elevation view of a portion of the bottom plate of the present invention illustrating a screw barrel having an angled first end and a riveted second end.
Figure 3:
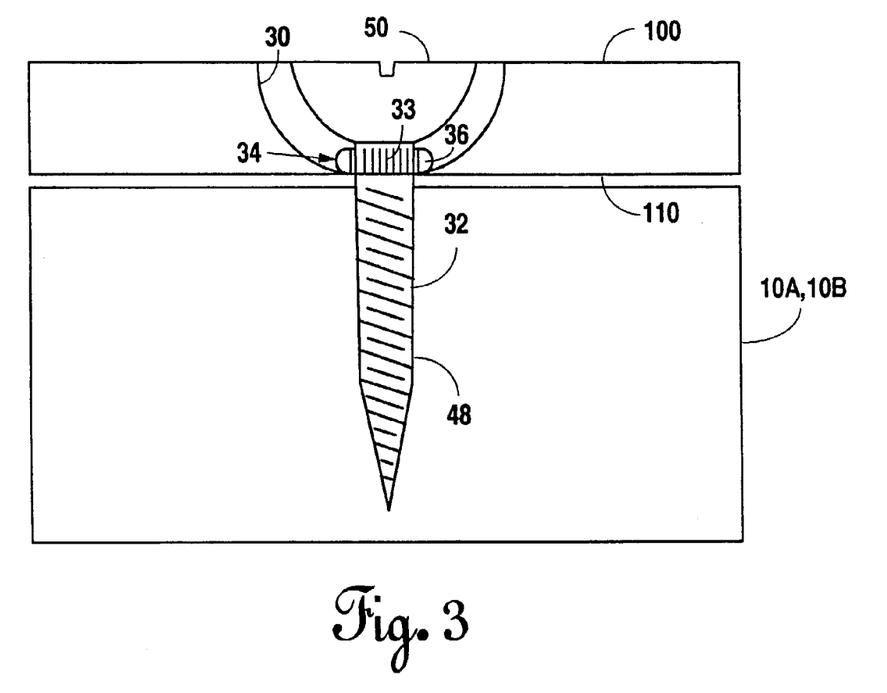
FIG. 3 is a side elevation view of an embodiment of the locking member of the present invention using a substantially circular locking ring attached to a substantially circular countersink.
Figure 3A:
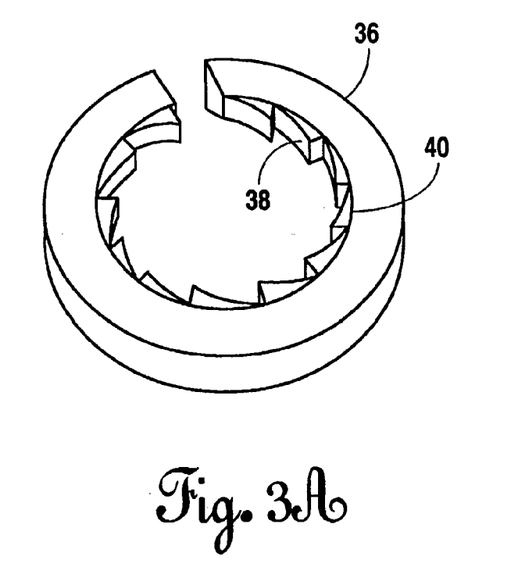
FIG. 3A is a perspective view of the locking ring of FIG. 3 illustrating the rachet teeth upon an interior surface of the locking ring.

Referring to FIGS. 1, 2 and 2A, the screw barrel (20) has an angled first end (20A) and a riveted second end (20B) in one embodiment of the present invention. The angled first end prevents disengagement of the screw barrel (20) from the opening (24) in the bottom base plate (19) by restricting movement of the screw barrel in a second direction toward the spinal cord (70).

Alternatively, the riveted second end (20B) of the screw barrel (20) prevents the disengagement of the screw barrel from the opening (24) by restricting movement in a first direction away from the spinal cord (70). The angled first end (20A) of the screw barrels also allows barrel screws (22) that are placed through the slots (28) of the top plate (26) to engage the screw barrels (20) of the bottom plate (18) at various angles. This allows the attachment of the medical appliance (100) to the bone segments (10A and 10B, respectively) to be stable and flexible.

The top plate (26) has a plurality of unique countersinks (30) for receiving special bone screws (32) such that the top plate may be attached to the outside surfaces (12A and 12B, respectively) of each bone segment (10A and 10B, respectively). The countersinks (30) are configured to receive bone screws (32) such that a bone screw inserted into a countersink may engage the outside surface (12A and 12B) of the bone segment thus attaching the top plate (26) to the bone segment. The first and second ends (26A and 26B, respectively) may be tapered such that no sharp edges may contact the body of the patient (not shown).

The top (26) and bottom plates (18) are composed of any strong, thin, non-porous material such as carbon fiber, modified carbon, titanium, surgically compatible steel, physiologically inert and/or medically compatible polymers such as urethane or DELRIN® polymers, or any other substantially rigid surgical implant or biologically compatible material. The top plate (26) is longer than the bottom plate (18) such that the top plate attaches to the outside surfaces (12A and 12B) of the bone segments and the bottom plate attaches to the ledge surface (14) of the bone segments (10A and 10B, respectively). Both the top plate (26) and the bottom plate (18) attach to each other and to the bone segments thus providing additional stability to the medical appliance (100).

When intervertebral fusion is desired, cancellous bone chips are formed into very fine particles such that they may be inserted and packed tightly into the space (72) between the bone segments. The cancellous bone chips then work in concert with the top (26) and bottom plate (18) of the medical appliance (100) to provide stability to the bone segments. An artificial disk may be used to fill the space between the bone segments and may be composed of any number of compressible physiologically inert and/or medically compatible polymers. For example, the disk may be composed of urethane or DELRIN® polymer for the purpose of providing shock absorption between the top plate (26) and the bottom plate (18).

Referring to FIGS. 3, 3A, 4 and 4A, the medical appliance (100) has a locking collar (34) disposed in each countersink (30). Each locking collar engages each bone screw (32) to the medical appliance (100) such that axial and rotational movement of each bone screw is restricted. In this embodiment of the present invention, the locking member (34) is a locking ring (36) having a plurality of tapered, rachet teeth (38). The rachet teeth are located on an interior surface (40) of the locking ring (36) such that when the locking ring is attached to a countersink (30) of the top plate (26), the teeth are engageable with a serrated neck (33) of the bone screw (32) when the bone screw (32) is inserted through the countersink (30). The interplay between the teeth (38) and the serrated neck (33) allows the bone screw (32) to be placed into the countersink and racheted into the bone segment. The bone screw is held in place by the teeth (38) once racheted into the bone segment. The taper of the teeth (38) of the locking ring (36) may be adjusted to vary the amount of torque required to remove the bone screw from the locking member (34).

Figure 4:
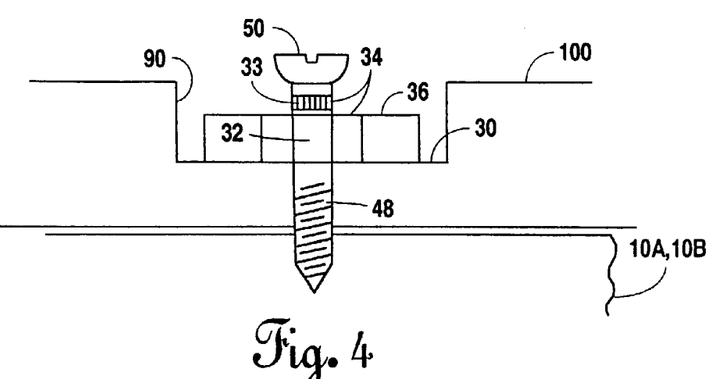
FIG. 4 is a side elevation view of an embodiment of the locking member of the present invention using a non-circular locking ring and a non-circular countersink.
Figure 4A:
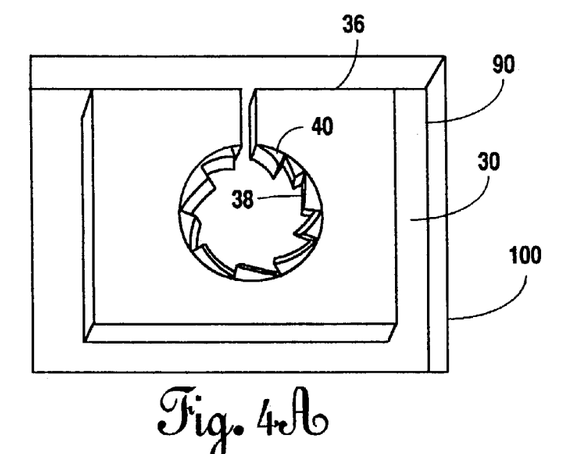
FIG. 4A is a perspective view of the locking ring of FIG. 4 illustrating the rachet teeth upon an interior surface of the locking ring.
Figure 4B:
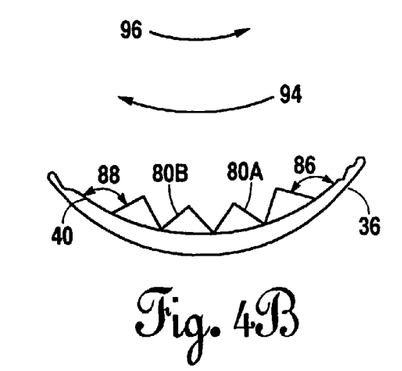
FIG. 4B is a top plan view of a portion of a locking ring illustrating the tapered rachet teeth.

Referring to FIG. 4B, each of the rachet teeth (38) has a leading edge (80A) and a trailing edge (80B). The taper of the leading edge (80A) controls the amount of torque required to rachet the bone screw (32) into the locking ring (36). The greater the taper of the leading edge (80A) above 90°, the less torque is required to insert the bone screw (32) into the locking ring (36) due to decreased resistance between the rachet teeth (38) and the serrations (33) of the bone screw (32).

Alternatively, the taper of the trailing edge (80B) controls the amount of torque required to rachet the bone screw (32) out of the locking ring (36). The greater the taper of the trailing edge (80B) above 90°, the less torque is required to remove the bone screw (32) from the locking ring (36) due to decreased resistance between the rachet teeth (38) and the serrations (33) of the bone screw (32). The taper angles of the leading and trailing edges (86 and 88, respectively) may be manipulated to provide varying degrees of stability for the bone screws (32).

Figure 5:
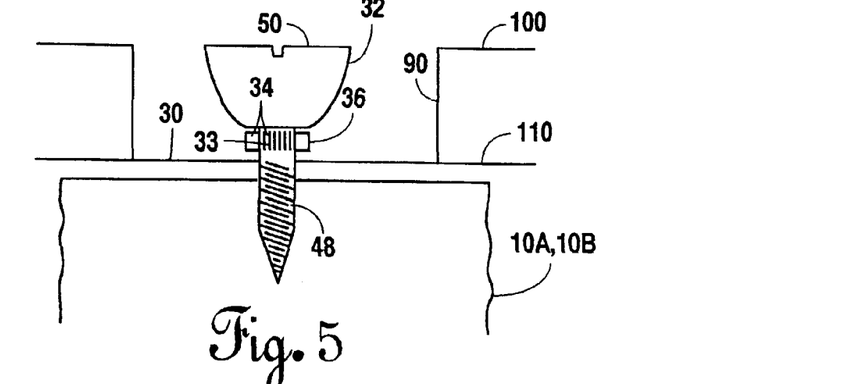
FIG. 5 is a side elevation view of an embodiment of the locking member of the present invention using a non-circular locking ring preassembled to the bone screw.

Both the locking ring (36) and the countersink (30) may have a substantially circular configuration or a non-circular configuration as illustrated in FIGS. 3–6. Referring to FIGS. 4, 4A and 5, one embodiment of the present invention uses a non-circular locking ring (36) having a plurality of tapered, rachet teeth (38) upon an interior surface (40) is used in conjunction with a non-circular countersink (30). The locking ring (36) may be attached directly to the bone screw (32) as a collar such that the teeth are engageable with a serrated neck (33) of the bone screw (32) upon insertion of the bone screw (32) through the countersink (30).

Figure 6:
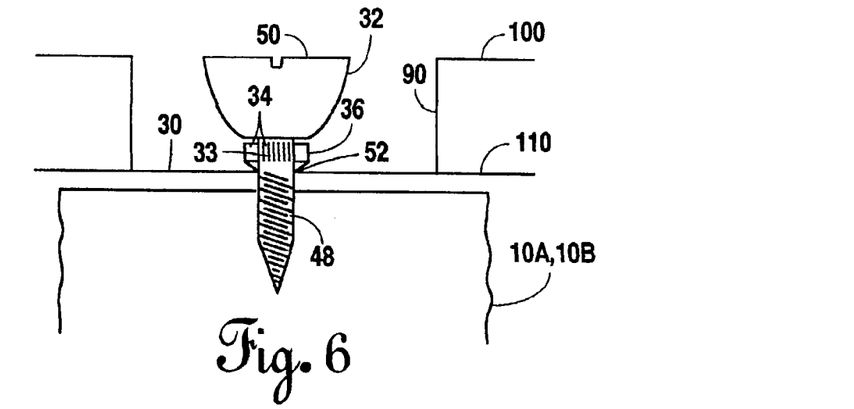
FIG. 6 is a side elevation view of an embodiment of the locking member of the present invention using a locking ring having an arcuate lower surface preassembled to the bone screw.

The locking ring rotates when the bone screw rotates due to the engagement of the teeth of the locking ring and the serrated neck of the bone screw (32). This non-circular configuration allows limited rotational movement of the bone screw without causing the bone screw to disengage from the bone segment. The locking ring (36) is sized slightly smaller than the countersink (30) such that the locking ring may rotate along with the bone screw until it abuts side wall (90) of the countersink. Referring to FIG. 6, another embodiment of the present invention uses a locking ring having an arcuate lower surface (52) that allows limited flexion of the bone segment (10A and 10B, respectively) about the appliance once the bone screw (32) has been inserted through the countersink (30).

Figure 7:
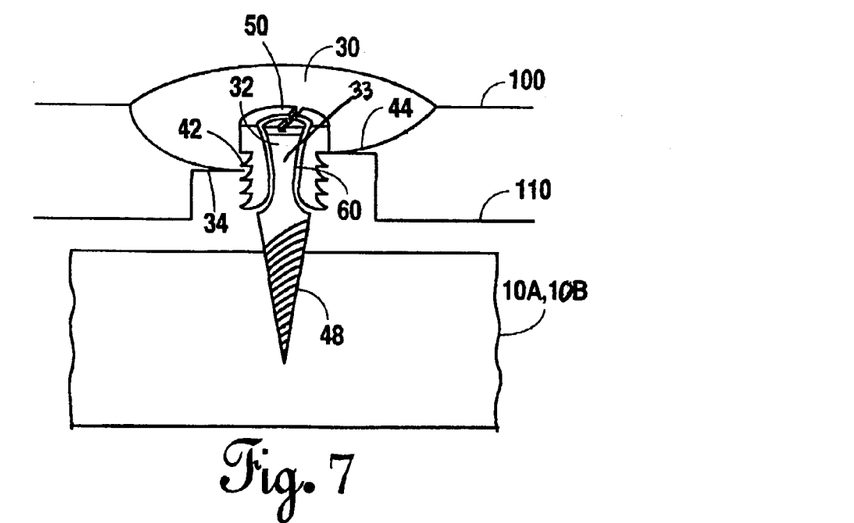
FIG. 7 is a side elevation view of an embodiment of the locking member of the present invention using a bone screw having a grooved collar for engaging a threaded inner surface of the countersink.

Referring to FIG. 7, another embodiment of the present invention uses a bone screw (32) having a threaded collar (42) for engaging a threaded inner surface (44) of the countersink (30) as a locking member (34). Engagement of the threaded inner surface of the countersink and the collar allows for attachment of the bone screw to the countersink (30) of the medical appliance (100) and provides for limited movement of the bone segment (10A, 10B) in relation to the appliance (100). An hour glass shaped orifice or gap (60) located between the collar and the bone screw (32) allows limited bone segment movement while the engagement of the collar (42) and the threaded surface (44) allows rotational movement even though the collar remains engaged with the threaded surface of the countersink (30). The number of threads present upon the threaded inner surface (44) may be varied to provide for additional stability or range of motion. To illustrate, an increase in the number of threads contained by the threaded inner surface (44) will increase the stability of the locking member by allowing only limited rotation. Alternatively, a decrease in the number of threads will increase the range of rotation available to the collar (42) within the threaded inner surface allowing rotation of the collar (42) within the threaded inner surface (44).

The locking system of the present invention may have a plurality of countersinks (30) located within the surface of the appliance (100). Each countersink (30) has an opening (60) for receiving a bone screw (32). The bone screw having a first threaded end (48), an opposite second head end (50), and a neck (33). The locking system also has a locking collar (34) for engaging the bone screw (32) to the medical appliance (100) at its neck (33) such that axial and rotational movement of the bone screw is restricted.

The bone screw (32) of the locking system may have a substantially spherical head end (50) or an hour glass shape (FIG. 7), or a convex spherical shape (FIGS. 7A–7C), or any other configuration that allows the screw to be secured to the countersink (30) of the medical appliance (100). Referring to FIGS. 3, 3A, 4, and 4A, in one embodiment of the present invention, the locking system of the present invention has a locking member (34) affixed in each countersink (30). Each locking member engages each bone screw (32) to the medical appliance (100) such that axial and rotational movement of each bone screw is restricted.

Figure 7A:
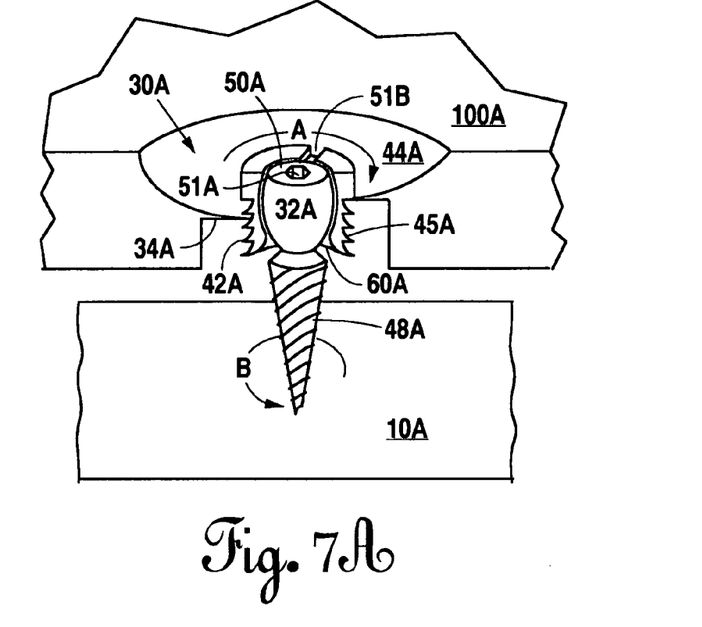
FIG. 7A illustrates a partial cutaway perspective view of a concave/convex screw head arrangement of the present invention.

Referring to FIG. 7A, yet another embodiment of the locking system of the present invention uses a substantially spherical or convex shaped bone screw (32A) having a threaded collar (42A) for engaging a threaded inner surface (44A) of the countersink (30A). Engagement of the threaded inner surface and the collar allows for attachment of the bone screw to the countersink (30A) of the medical appliance (100A) and provides for limited movement of the collar (42A) with respect to the countersink (30A). A concave orifice (60A) located between the collar and the bone screw (32A) allows limited axial and flexion movement while the engagement of the collar (42A) and the threaded surface (44A) allows rotational movement of the screw collar even though the collar remains engaged with the threaded surface of the countersink (30A). It has been determined that when the outer shape of the head (50A) of the bone screw (32A) is convex and the orifice (60A) in the collar (42A) is concave, there is improved retention of the screw (32A) within the collar (42A) and the collar (42A) within the countersink (30A).

Figure 7B:
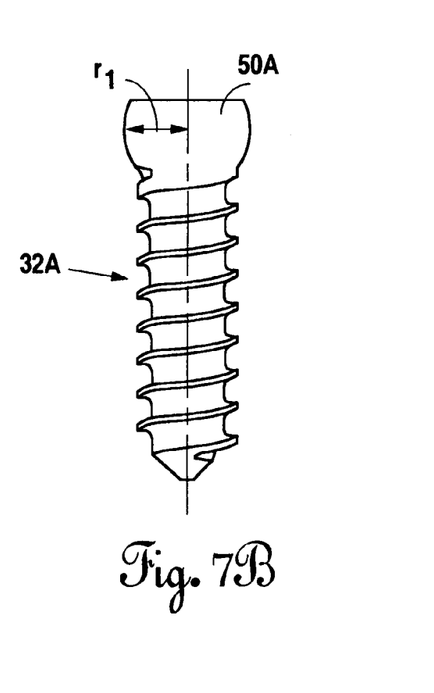
FIG. 7B shows a side elevation plan view of a bone screw of the embodiment of FIG. 7A.
Figure 7C:
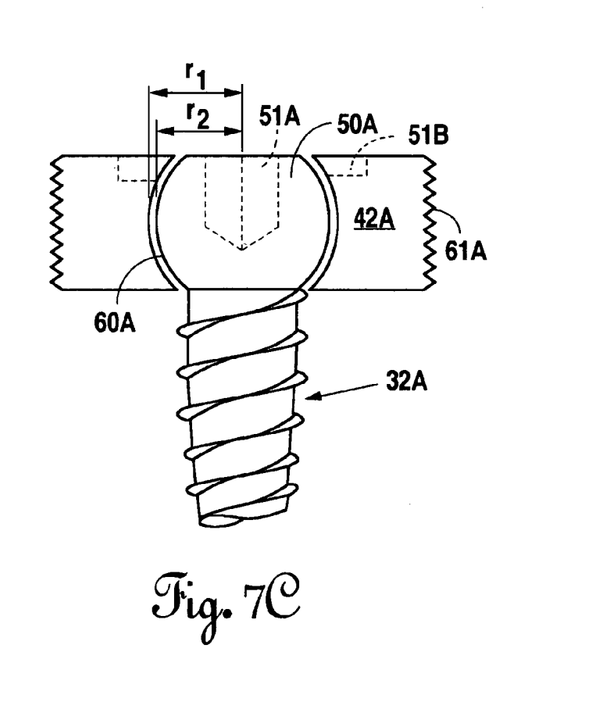
FIG. 7C is a partial cross-section view of the screw and collar arrangement of the embodiment of FIG. 7A.

FIG. 7B illustrates a bone screw (32A) as discussed above wherein the head (50A) is provided with a convex, generally spherical radius $r_1$ of approximately 0.10". As shown in FIG. 7C, radius $r_1$ cooperates with a corresponding inner, concave radius $r_2$ of the orifice (60A) to limit axial and flexion movement of the screw collar (42A) while the collar (42A) remains engaged in the countersink (30A). Again, this particular cooperating convex/concave relationship improves retention of the screw in this locking system.

The number of threads present upon the threaded inner surface (44A) may be varied to provide for additional stability or range of motion. To illustrate, an increase in the number of threads contained by the threaded inner surface (44A) will increase the stability of the locking member by allowing only limited rotation. Alternatively, a decrease in the number of threads will increase the range of rotation available to the collar (42A) within the threaded inner surface allowing rotation of the collar (42A) within the threaded inner surface (44A).

It is understood that each embodiment of the locking system described above may be used in combination with the apparatus described above or to affix any other medical appliance (100) to bone. The medical appliance (100) may be affixed to spaced apart bone segments (10A and 10B, respectively) by following a few simple steps as outlined in U.S. Pat. No. 6,402,755, included herein by reference.

To facilitate the insertion of the insertion locking system of the embodiments of FIGS. 7 and 7A, a unique wrench has been developed.

Figure 8A:
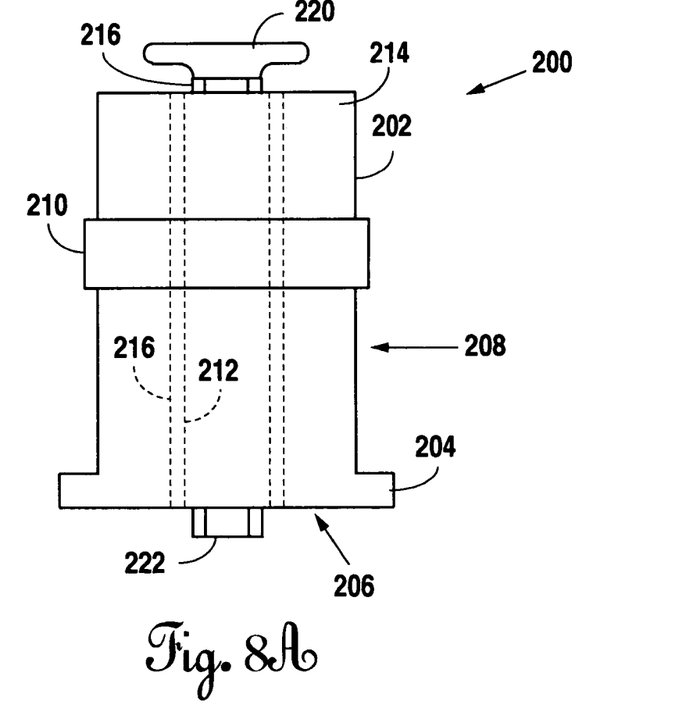
FIG. 8A is a side elevation view of the wrench of the present invention.

In FIG. 8A, wrench (200) has a generally cylindrical outer barrel housing (202) with outwardly extending blades (204) at the base (206) of the barrel. Around a central portion (208) is a grip member which is used to rotate the outer barrel (202) and the blades (204).

The barrel (202) has an inner orifice (212) extending from a top end (214) through the base (206). An elongated, generally cylindrical rod (216) extends through the orifice (212) with a handle member (220) on a top end and a screw face (222) on the opposite, bottom end. The screw face extends out of the orifice (212) and beyond the base (206). In one embodiment of the wrench, the rod and screw face are similar to a traditional Allen wrench with a number of flat surfaces which engage the flat surfaces of a cooperating Allen head screw. It should be understood that the rod and screw face may be other cooperating configurations including a socket wrench-like configuration well known in the fastener art.

Figure 8B:
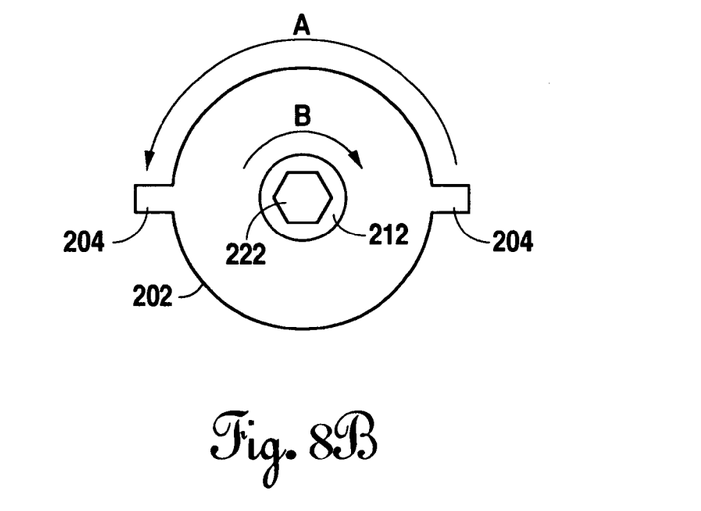
FIG. 8B is a bottom plan view of the wrench of FIG. 8A showing opposite directions of rotation for the central rod and the outer barrel of the wrench.

FIG. 8B illustrates a bottom end view of the wrench (200) showing the arrangement of the screw face (222) and blades (204). It should be readily understandable that when the bone screw (32A) (FIG. 7A) of the present locking system has an Allen-type recess (51A) in the screw head (50A), the screw face (222) has a complimentary Allen-type projection for rotation of the screw (32A). However, in order to tighten the collar portion (42A) within the countersink (30A), the blades (224) engage the slot (51B) in the top face of the collar (42A)

Thus, by the gradual tightening of the screw (32A) separately from the tightening of the collar (42A), the locking system is utilized to engage the screw with the bone segment. It has been found that when the threads of the screw (48A) and the threads of the collar (45A) are opposite hand, the likelihood of the screw loosening from the bone segment is considerably reduced. (See disectional arrows A and B in FIGS. 7A and 8B.)

As previously stated, while the threads (48A) of the screw (32A) and the collar threads (42A) may be the same hand, the threads per millimeter of the screw are different than the threads per millimeter of the collar (42A). This will achieve a degree of improved retention of the screw in the bone segment while allowing the desired movement of the screw within the concave gap (60A) between the screw head (50A) and the inner walls of the collar cavity.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

What is claimed is:

1. A locking system for attaching a workpiece to bone comprising:
    a countersink in said workpiece, said countersink having an opening for receiving a bone screw having a first end threaded in a first direction, an opposite head end, and a collar having external threads, said collar rotatingly affixed to a neck section of said screw; and
    complimentary locking threads in said countersink for engaging said collar to said workpiece at said neck section such that axial and rotational movement of said bone screw is restricted when said workpiece is affixed to said bone, said complimentary locking threads threaded in a second direction opposite said first threaded direction of said bone screw.

2. The locking system of claim 1, wherein said head end is substantially spherical.

3. The locking system of claim 2 wherein said threaded collar has a concave screw head retaining cavity, said substantially spherical head end of said bone screw adapted to be rotatingly secured within said cavity.

4. The system of claim 1 further comprising a wrench having an outer body with outwardly extending blades and an inner rod rotatably extending through an inner passage of said body, said rod having a screw face portion extending beyond a base of said body and adapted to engage said opposite head end of said bone screw, said blades adapted to engage a slot in a top face of said collar.

5. A fastener system for joining a first workpiece to a second workpiece comprising:
    a screw having a head and a body section threaded in a first direction, said head having a top section to facilitate rotation of said screw; and
    a locking collar having a top surface, a top opening, a bottom opening, a smooth, concave inner cavity, and a outer wall threaded in a second direction opposite said first direction of said screw body section, said threaded outer wall cooperating with a complimentary threaded inner surface of a collar receiving opening in said first workpiece to releasably secure said collar in said first workpiece when said collar is rotated in said collar receiving opening in said second direction of said threaded outer wall, said inner cavity adapted to rotatingly retain and hold said head of said screw with said head top section exposed through said top opening and said threaded body section of said screw extending outwardly from said bottom opening sufficiently to engage and join said second workpiece when said head of said screw is rotatably urged against said second workpiece in said first direction of said threaded body section.

6. A fastener system of claim 5 further comprising a wrench having an outer body with outwardly extending blades, an inner rod rotatably extending through an inner passage of said body, said rod having a face portion extending beyond a base of said body and adapted to engage said top section of said head of said screw, said blades adapted to engage a slot in said top surface of said locking collar.

* * * * *